United States Patent
Baffoni

[19]

[11] Patent Number: 6,119,806
[45] Date of Patent: *Sep. 19, 2000

[54] MULTIPLE PHASE ACOUSTIC SYSTEMS

[76] Inventor: Frank A. Baffoni, 65 Ann Dr., East Greenwich, R.I. 02818

[ * ] Notice: This patent issued on a continued prosecution application filed under 37 CFR 1.53(d), and is subject to the twenty year patent term provisions of 35 U.S.C. 154(a)(2).

[21] Appl. No.: 08/881,211

[22] Filed: Jun. 24, 1997

[51] Int. Cl.[7] .................................................. A61B 7/02
[52] U.S. Cl. ............................................ 181/131; 181/137
[58] Field of Search ................................... 181/131, 137, 181/148, 151, 156, 199, 175

[56] References Cited

U.S. PATENT DOCUMENTS

| | | | |
|---|---|---|---|
| 2,389,868 | 11/1945 | Olson | 181/131 |
| 4,101,736 | 7/1978 | Czerwinski | 181/151 |
| 4,270,627 | 6/1981 | Hill | 181/131 |
| 4,387,784 | 6/1983 | Hill | 181/131 |
| 4,657,108 | 4/1987 | Ward | 181/151 |
| 4,714,133 | 12/1987 | Skaggs, Jr. | 181/151 |
| 4,776,426 | 10/1988 | Kazama | 181/131 |
| 4,889,208 | 12/1989 | Sugihara | 181/148 |
| 5,281,777 | 1/1994 | Alton, Jr. | 181/151 |

*Primary Examiner*—Khanh Dang
*Attorney, Agent, or Firm*—Hale and Dorr LLP

[57] ABSTRACT

An acoustic device has first and second conduits such that the first conduit has an inlet and an outlet, and the second conduit encloses a material that is different from the material in the first conduit, or encloses the same material as that in the first conduit but at a different pressure. The first and second conduits share a common wall that is made up of a flexible membrane that allows acoustic signals in the first and second conduits to be acoustically coupled together, thereby allowing acoustic signals in the first conduit to be altered to suppress, enhance, or change certain aspects of the acoustic signal without the use of electronics.

45 Claims, 6 Drawing Sheets

MULTIPLE PHASE ACOUSTIC SYSTEMS

This invention relates generally to acoustic systems, and is related to my previous U.S. Pat. No. 5,530,212, issued Jun. 25, 1996, which is expressly incorporated by reference for all purposes.

BACKGROUND OF THE INVENTION

It is generally well-known that acoustic signals can be manipulated by converting them to electronic signals with a transducer, such as a microphone, and then altering those electronic signals before they are provided to a sound providing device, such as a speaker. For example, many stereos have an equalizer that can be used to enhance or suppress signals any of a number of desired frequency ranges. In some situations, it may be desirable to enhance or suppress certain features of an acoustic signal, but it may not be practical or desirable to accomplish such enhancement or suppression electronically. For example, as noted in the incorporated patent, in the case of a stethoscope, a medical practitioner may not want to run the risk of electronic problems or low batteries at an inconvenient time. Consequently, it would be desirable to be able to enhance and/or suppress aspects of acoustics signals in a non-electronic manner.

SUMMARY OF THE INVENTION

This invention relates to the manipulation of acoustic signals generally by enhancement and/or suppression of desired aspects without requiring that the acoustic signals first be converted to electronic signals. The devices of the present invention direct sound through multiple conduits having different phases (i.e., solid, semisolid or gel, liquid, or gaseous media). In these devices, acoustic signals in a first conduit with a first phase interact across a flexible membrane with signals traveling through a second conduit. The first conduit is preferably at ambient conditions, while the second conduit is sealed from the first conduit and encloses a different material and/or has a different pressure from the material and/or pressure in the first conduit. The interaction across the membrane produces a final acoustic signal that is thus enhanced by the sum total of the interacting sounds across the membrane.

In these embodiments, the first conduit receives an acoustic signal at an inlet end. The first conduit may or may not have an outlet, while the second conduit may have an inlet, an outlet, both an inlet and an outlet, or neither an inlet nor an outlet. In the case where the second conduit does have an inlet and/or an outlet, and where the second conduit is sealed from ambient conditions, the inlet and/or the outlet for sound can be provided through the use of a diaphragm so that the material in the conduit remains sealed from the ambient environment. In each case, the inlet of the first conduit can be open to ambient conditions to receive ambient acoustic signals, can receive signals from directing the inlet and to a desired location (such as in a stethoscope), or can receive signals provided at one end of the first conduit with a sound providing device, such as a speaker. Specific examples of the use of such multiple phase conduits in an acoustic system include a stethoscope and a loudspeaker.

The principles of the present invention can also be used in other applications, including sensing, detection, carrying acoustic energy, and propulsion. In the sensing context, an object can be placed in a conduit and sound can be introduced at one end and detected at another. The changes in the sound are used to determine characteristics of the object. For detecting and measuring, a material can be provided to a second conduit while sound is provided through a first conduit, with the first and second conduits being separated by a flexible membrane. In this case, as the composition, volume, or some other characteristic of the material in the second conduit changes, the changes can be sensed by changes in the detected should in the first conduit. In another application, a pair of conduits can be provided together and used with ultrasonic energy. In one particular application, the conduits can be provided together in a catheter in which ultrasonic energy is used to break up gall stones. With the second conduit, certain aspects of the ultrasonic energy can be enhanced or suppressed. For propulsion, an object traveling in a fluid media is propelled by an acoustic transducer, while compartments with flexible membranes enclose material that alters the effects of the energy from the acoustic transducer.

The resultant final sound thus can be acoustically enhanced to convey particular and useful information from its component sounds. This enhancement may include shaping of the final sound in terms of waveform, frequency, and amplitude, without the use of electronic manipulation. These characteristics of the final sound can be specified based on the material used, the geometric characteristics of the conduits, flexible membranes, and diaphragms, pressures of material in the conduits, the composition of the membrane and conduits, and the interaction between the conduits as they form the final sound. For example, a material may have effects on the sound at higher or lower frequencies, in which case, the flexible membrane and second conduit can be considered to be like a high or low pass acoustic filter that operates on the sounds themselves rather than on an electronic representation of the sounds. The final sound created in this manner may be used to convey acoustic information to the listener, or to a suitable sensing device. Other features and advantages will become apparent from the following detailed description, drawings, and claims.

DETAILED DESCRIPTION

FIGS. 1–4 are each cross-sectional views of acoustic devices with two elongated conduits separated by a flexible membrane. In each case, a first elongated conduit is open to ambient conditions, while a second elongated conduit is sealed from the first conduit and has a pressure or material that is different from that in the first conduit, i.e., it is different from the ambient air conditions in this case. These embodiments differ based on whether the second conduit has an inlet and/or an outlet.

Figure 1:
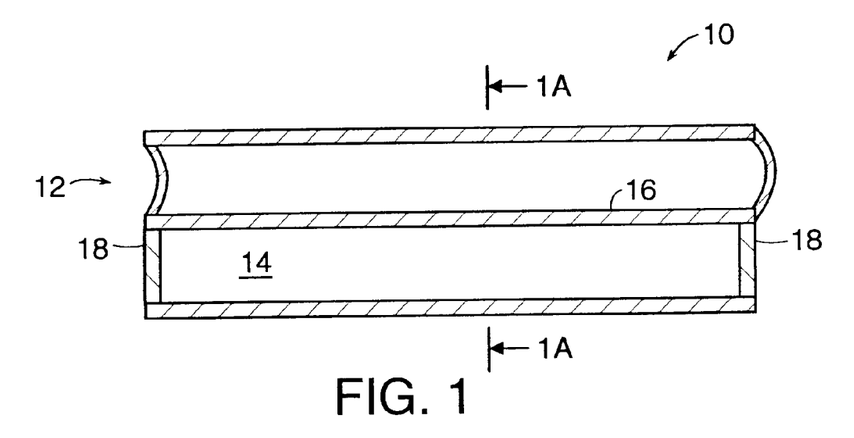
FIGS. 1–4 are cross-sectional views of acoustic devices according to the present invention.
Figure 1A:
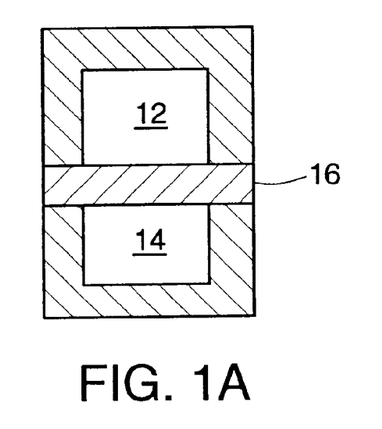
FIG. 1A is a cross-sectional view taken through section lines 1A—1A in FIG. 1.

Referring to FIG. 1, an acoustic device 10 has a first conduit 12 and a second conduit 14, separated by a flexible membrane 16. The conduits have different phases, with first conduit 12 having air at ambient conditions, and the second conduit having either different material, whether a gas, liquid, gel, or solid, or the same material (air, in this example) at a different pressure.

Each conduit has its own respective acoustic outlet that can present an acoustically coupled signal to a listener or listening device. Second conduit 14 has diaphragms 18 at each end serving as acoustic inlets and outlets. The second conduit thus also receives and provides acoustic signals; additionally, the sounds in the conduits interact (i.e., are acoustically coupled) across the flexible membrane. The resulting outlet sounds are therefore the result of each of the individual acoustic signals and the acoustic coupling.

Figure 2:
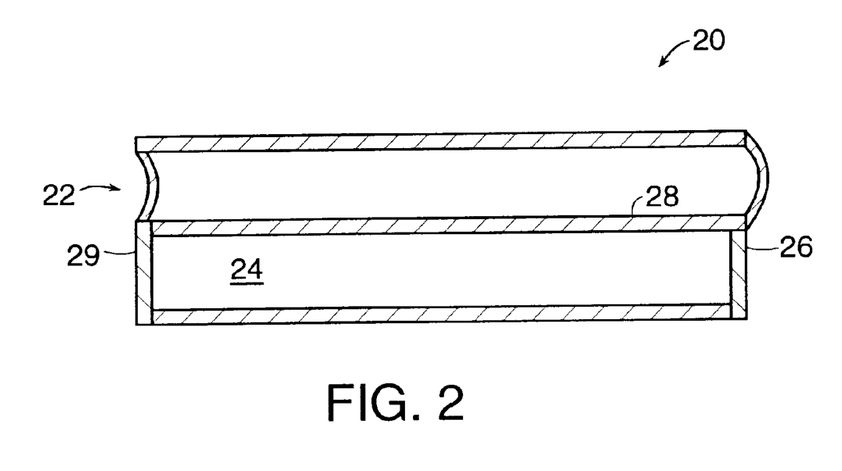

Referring to FIG. 2, a second device 20 has first and second conduits 22 and 24, separated by a flexible membrane 28. Second conduit 24 has a diaphragm 29 at an inlet end, but second conduit 24 terminates in a blind end 26 at the outlet side. The second conduit acoustic signal modifies the signal in the first conduit via flexible membrane 28. This combined acoustically coupled signal then exits only first conduit 22.

The stethoscope in the incorporated U.S. Pat. No. 5,530,212 is an example of the embodiment of FIG. 2, except that the embodiments of the stethoscope have a diaphragm at the inlet end of the first conduit. As is shown in that patent, a diaphragm can have two chambers, and the sound can interact along the flexible membrane, but one of the chambers is sealed to ambient conditions, while the other provides sounds to the listener through earphones.

Figure 3:
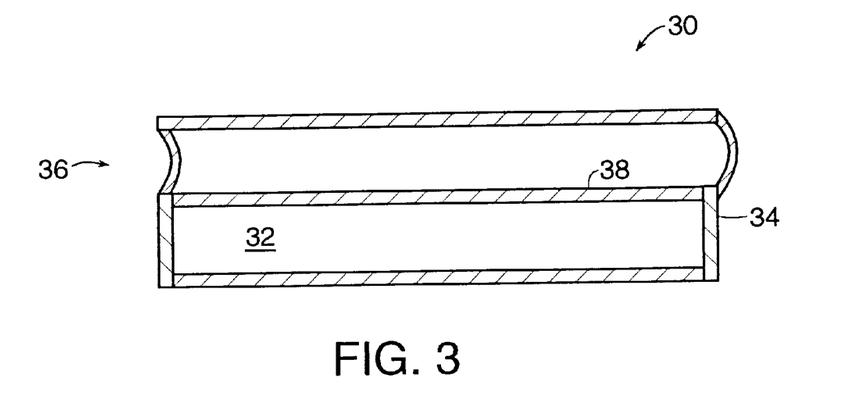

FIG. 3 illustrates a third device 30 with a first conduit 36 and a second conduit 32. Conduit 32 does not have its own acoustic input signal, but it does have a diaphragm 34 for an outlet. The signal generated in first conduit 36 is acoustically coupled to the signal in second conduit to create an acoustically different signal in the second conduit via a flexible membrane 38. Each conduit has its own dedicated acoustic outlet. In this case, each acoustic outlet can be presented to the listener.

Figure 4:
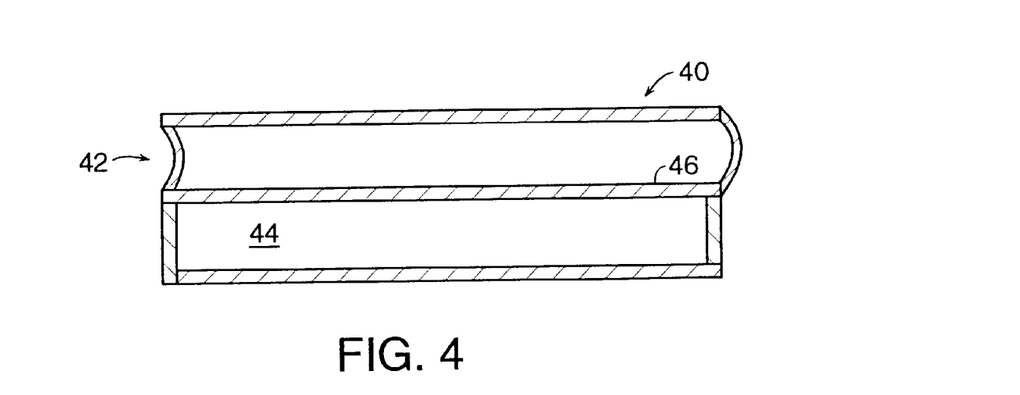

FIG. 4 shows a fourth device 40 in which a first conduit 42 has an inlet and an outlet, and is acoustically coupled to a second conduit 44 across a flexible membrane 46. The signal generated in the second conduit modifies the acoustic signal in the first conduit through its interaction across the flexible membrane, which thus serves as an acoustic transducer. Second conduit 44 does not have a separate inlet or outlet.

In each of the embodiments of FIGS. 1–4, first conduit 12, 22, 36, or 42, respectively, is shown with an open inlet and an open outlet. In each of these cases, however, the outlet end can be closed with either a flexible end, such as a diaphragm, or with a blind end. In the case of the blind end, sound that is introduced at the inlet side is reflected back from the blind end. In this case, the sound that is provided at the inlet end interacts with the second conduit via the flexible membrane in both directions. Moreover, the inlet end can have a diaphragm for providing the acoustic signal in the first conduit.

In each of the embodiments of FIGS. 1–4, a source of an acoustic signal is provided outside the acoustic device at an inlet end. As the sound is introduced into the first conduit, the flexible member will tend to flex away from the first conduit and "into" the second conduit, with the amount and characteristics of the flexing depending on the material and pressure in the second conduit, the physical characteristics of the second conduit, and the characteristics of the membrane. Alternatively, however, a separate source can be provided within the second conduit so that the membrane can flex "out" from the second conduit and into the first conduit. Depending on the characteristic of the sound input to the first conduit and the sound provided within the second conduit, the flexing of the membrane can occur in both directions at different times, or in different directions at different portions of the membrane.

In each case, the material and/or pressure selected for use in the second conduit is selected for its effect on the sound in the first conduit. A material may be selected, for example, because of a tendency to suppress or enhance low frequency or high frequency acoustic signals in analog waveforms, rather than as electronic signals.

Figure 5:
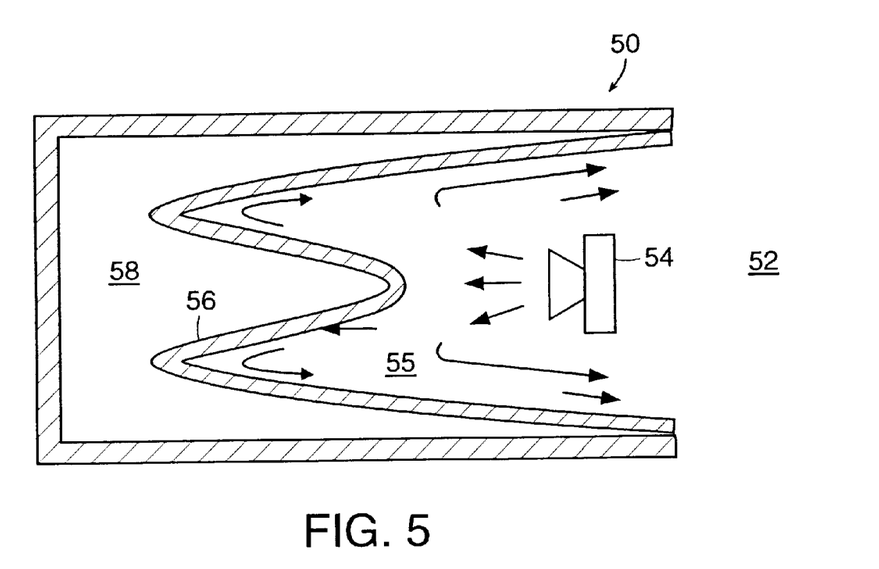
FIG. 5 is a cross-sectional view of a loudspeaker according to the present invention.

Referring to FIG. 5, a multiple phase acoustically coupled loudspeaker 50 is an application of the device of FIG. 4. Loudspeaker 50 provides sound to an external environment 52 by way of a transducer (i.e., speaker 54). Sound is initially created by speaker 54, which is powered by an electronic amplifier (not shown). Speaker 54 creates sound in the adjacent area 55 at one atmosphere in what serves as a first conduit. The sound in this first conduit induces sound in a region that serves as a second conduit 58 and has a solid, semisolid or gel, liquid, or gaseous (different from air) medium, or it can have air but at a pressure other than one atmosphere. The first conduit is acoustically coupled to the second conduit via a flexible membrane 56. This sound in this second conduit can move in an opposite direction, i.e., from conduit 58 to the first conduit across flexible membrane 56, thus modifying the overall sound in the first area. This acoustically coupled sound in is then presented to the listener.

In the embodiments shown above, the inlets to the first conduit are preferably open to the ambient environment. Alternatively, however, at the inlet end of the first conduit, a device, such as a speaker, can be disposed for providing an inlet acoustic signal. The conduits can have different geometries, but an elongated shape, with long length compared to diameter, may be desirable to maximize the effect from the membrane over the length of the conduits.

Variations of the embodiments of FIGS. 1–4 are shown in FIGS. 6–9. In each embodiment, one or two acoustic sources, represented as speakers, provide signals to the first and second conduits.

Figure 6:
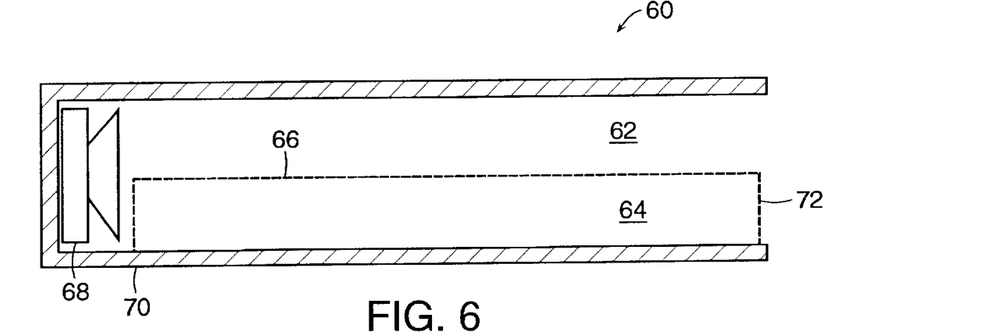
FIGS. 6–9 are cross-sectional views of acoustic devices according to further embodiments of the present invention.

Referring to FIG. 6, a device 60 has a first conduit 62 and a second conduit 64 separated by a flexible membrane 66. At an inlet end of both conduits is a speaker 68 for providing an acoustic signal to both conduits. As in the embodiments of FIGS. 1–4, second conduit 64 is sealed from first conduit 62 by membrane 66 and from the inlet and outlet with a flexible diaphragms 70 and 72. The second conduit has a material and/or pressure that is different from that in first conduit 62.

Figure 7:
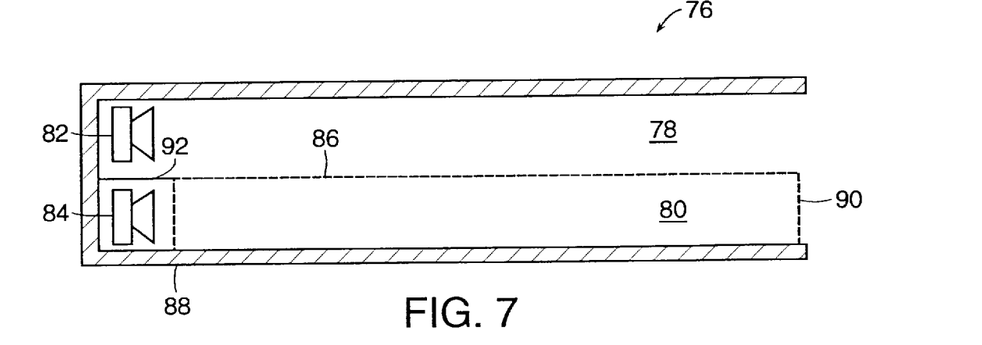

Referring to FIG. 7, a device 76 is generally similar to that in FIG. 6 with the first conduit 78, a second conduit 80, and a flexible membrane 86 between the conduits. Flexible diaphragms 88 and 90 are provided at the inlet and outlet ends of second conduit 80. The device has a first speaker 82 for providing an acoustic signal to first conduit 78, and a second speaker 84 for providing a second acoustic signal to second conduit 80 through diaphragm 88. A barrier 92 is provided between first speaker 82 and second speaker 84 to help prevent the sounds from mixing prior to being provided on opposite sides of membrane 86. With the device in FIG. 7, separate signals can be coupled into the first and second conduits, and thus membrane 86 can flex in either direction depending on the input acoustic signals.

Figure 8:
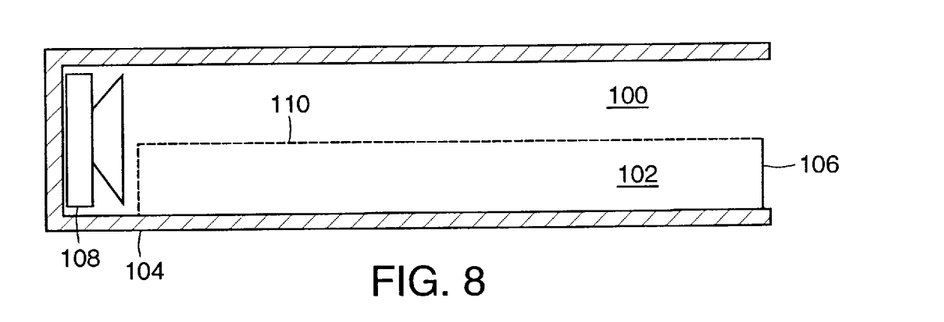

FIG. 8 shows another embodiment similar to that of FIG. 6 with a first conduit 100 having an open inlet end and an open outlet end, a second conduit 102 having a diaphragm 104 at its inlet end and a closed outlet end 106. A single speaker 108 provides an acoustic signal to both the first and second conduits. The first and second conduits are separated by a flexible membrane 110.

Figure 9:
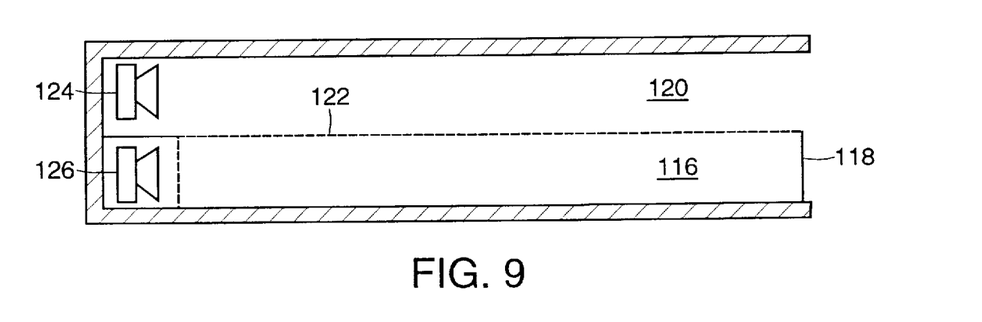

FIG. 9 shows an embodiment similar to that of FIG. 7, except that a second conduit 116 has a closed end 118. This device also has a first conduit 120, a flexible membrane 122, and first and second speakers 124 and 126.

In addition to the use of the present invention as a stethoscope and as a loudspeaker, the principles set out above can be applied to other devices. For example, in addition to providing an audible sound (i.e., 20 Hz–20 kHz), a device can be used to also provide an ultrasonic signal. For instance, an example of the ultrasonic application is the use of a catheter that can placed endoscopically, e.g., through the ampulla of vater in the duodenum (a part of the small intestine) and into the cystic duct that connects the gall bladder to the small intestine. An ultrasonic signal can be used, for example, to dislodge small gall stones stuck in the cystic duct, or to fracture these gall stones which might reside in the duct or the gall bladder itself. The catheter can have two conduits, separated by a flexible membrane, with one conduit serving to enhance or suppress aspects of the ultrasonic signal. The catheter can thus be generally similar to the embodiments shown above, such as that shown in FIG. 4.

Figure 10:
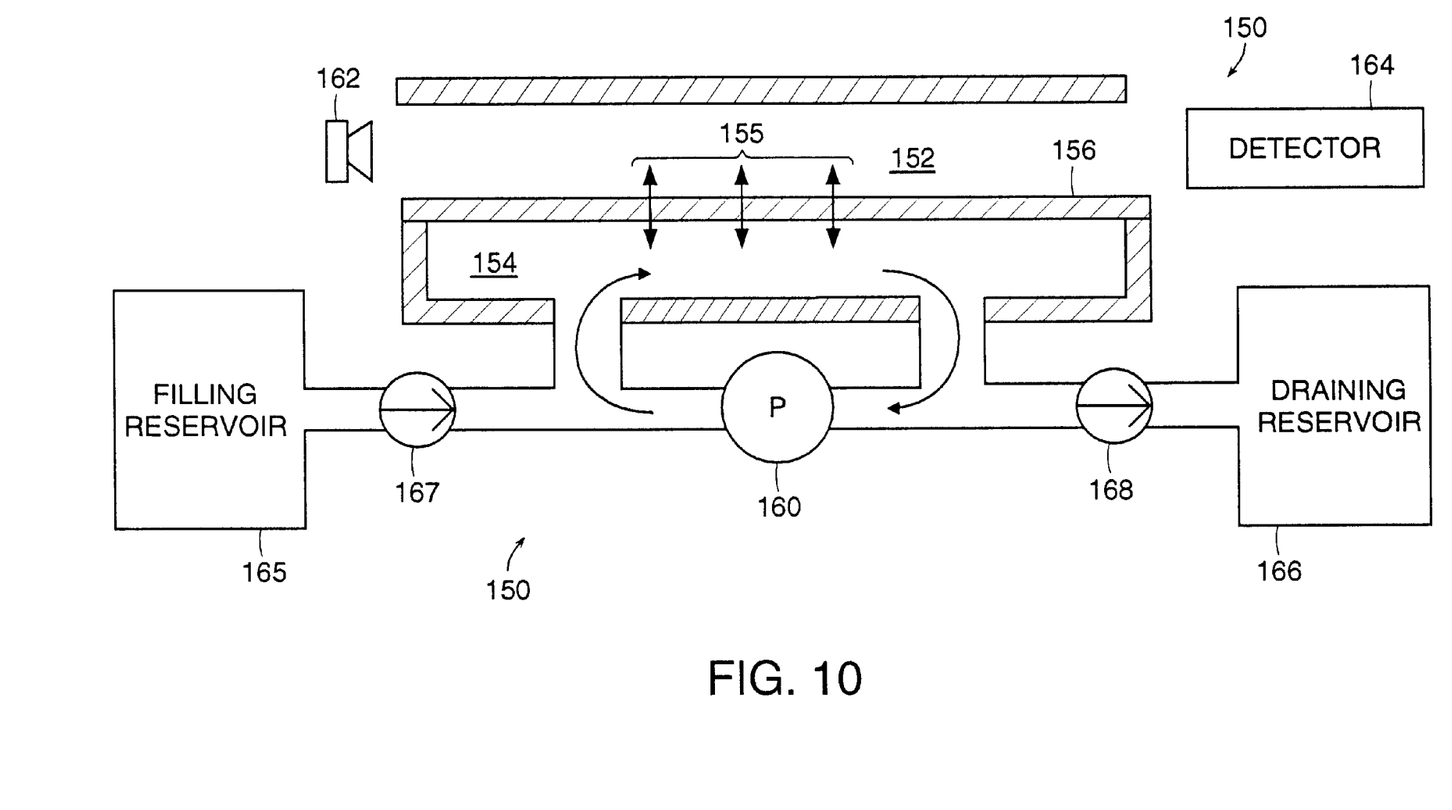
FIG. 10 is a cross-sectional view of an acoustic device used for sensing a fluid.

Referring to FIG. 10, in yet another application of the device of the present invention, a sensing device 150 has a first conduit 152 open to air, while a second conduit 154 is separated from the first by a flexible membrane 156. The second conduit has a material that is moved through the second conduit with a pump 160. Sound is introduced from a source 162 into first conduit 152 in order to provide non-invasive sensing. The sound provided at the inlet end is sensed by a detector 164 at the outlet end. The sound received at the outlet end will change depending on the characteristic of the fluid in the second conduit because the flexing of membrane 156 will change as indicated by arrows 155. Accordingly, the acoustic signals in the first conduit can thus be used to non-invasively sense physical characteristics of the material circulated in the second conduit, a change in the circulation, and any other sufficiently measurable change in characteristics. Alternatively, with sufficient acoustic energy, the source can be used to affect the fluid and/or its flow.

Other components of this system for controlling the flow of the liquid include a filling reservoir 165 for holding the fluid, a draining reservoir 166 for draining the fluid, and first and second one-way servo-controlled valves 167, 168 for controlling flow from reservoir 165 and to reservoir 166.

Figure 11:
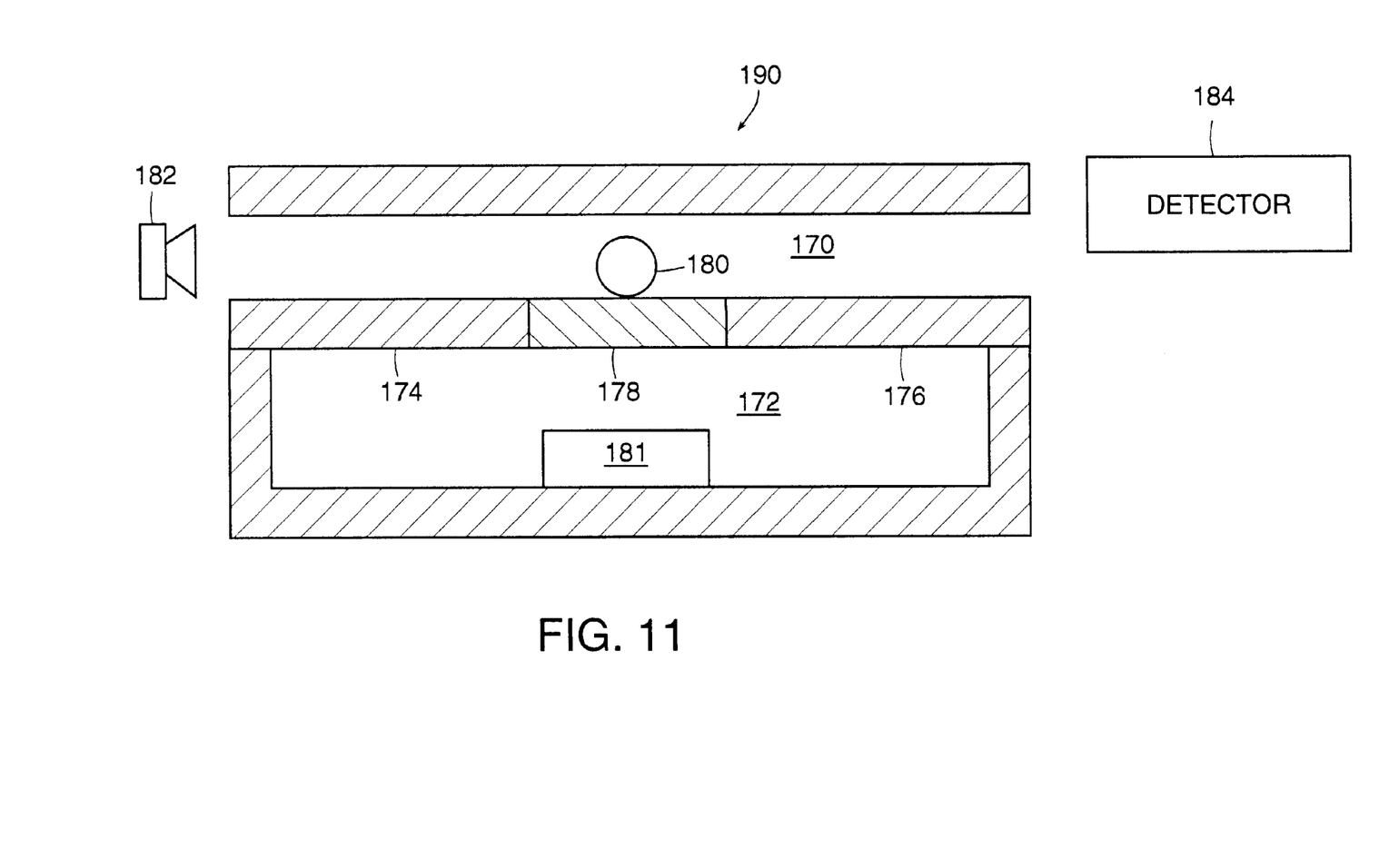
FIG. 11 is a cross-sectional view of an acoustic device used for sensing an object.

In another embodiment shown in FIG. 11, a sensing device 190 has first and second conduits 170, 172 separated by flexible membranes 174, 176, and also by a relatively rigid, non-flexible support portion 178, which may be located in the middle of the conduits along the lengthwise direction. Membranes 174, 176 are flexible on either side of support portion 178.

An object 180 to be detected can be provided on support portion 178, while sounds are introduced from an acoustic source 182 at the inlet end and detected by a detector 184. The detected sound at the outlet end will be a function of the object that is placed in the center. An additional detector 181 could also be placed inside the second conduit. The characteristics of the object can be sensed from the detected sound, include the shape, texture, and composition of the object. In case the object changes over time, such variations over time can be sensed. This support portion to produce a sensing device can be used with any of the embodiments of FIGS. 1–4 and 6–9.

In another application of the principles discussed above and referring to FIG. 12, a three-dimensional capsule 200 can be propelled through a fluid through the use of a transducer 202 that serves as an acoustic energy source for providing energy to a rear diaphragm 204. The capsule houses one large chamber, within which are one or more compartments 208, 210 that are made of a flexible material as a housing 212, 214, respectively. The pulsed acoustic signals in the embodiment of FIG. 12 can move along three paths–a first path 220 between compartments 208, 210, and second and third paths 222, 224 between compartments 208, 210 and an inner housing 228, respectively.

Figure 12:
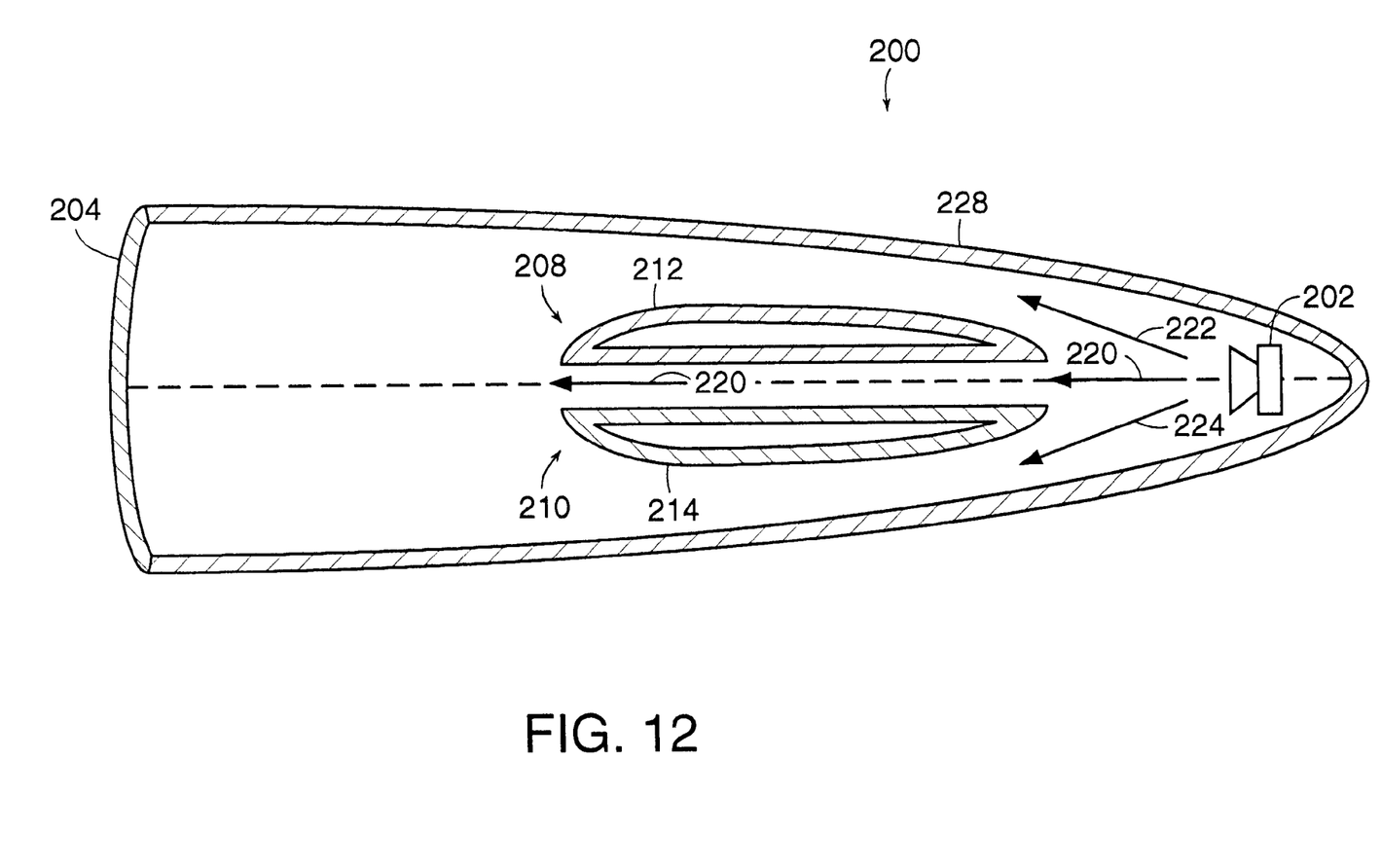
FIG. 12 is a cross-sectional view of an acoustic device used for propelling an object.

The composition of the flexible membranes and the material enclosed in compartments 208 and 210 can be selected to enhance or suppress characteristics of the acoustic energy in terms of amplitude, frequency, wavelength, etc. The final acoustic signal then moves flexible diaphragm 204 in and out in a pulsing fashion.

While the embodiments show above have generally been shown as having two conduits positioned side by side, many different geometries could be used, including coaxial arrangements with cylindrical or semi-cylindrical membranes, or with membranes having other shapes. The fact that the membrane can take a different shape is illustrated, for example, in the device of FIG. 5.

In the embodiments above, the flexible membrane can be a material that sufficiently seals the first conduit and the second conduit and also is sufficiently flexible to provide for the transmission of sound to accomplish these, for example, various types of thin plastic sheets could be used. In any event, the flexible membrane and diaphragms as used in terms of its geometry and as used with the other conduits, should be sufficiently flexible to respond to the acoustic signals and energy that is provided from the acoustic source(s).

Having described embodiments to the present invention, it should be apparent that modifications can be made without departing from the scope of the invention as defined by the appended claims. For example, while the embodiments above show two conduits, three conduits could be used with a first conduit having an inlet and an outlet being disposed being second and third conduits and sharing two common walls, each with a flexible membrane, with a respective second and third conduit. An example of the use of three conduits is shown, for example, in the incorporated stethoscope patent, as well as in the propulsion device of FIG. 12.

What is claimed is:

1. An acoustic device comprising:
    a first elongated conduit having an inlet end and an outlet end;
    a second elongated conduit that shares a common wall with the first conduit along a lengthwise direction, the common wall being made from a flexible membrane sufficiently flexible to flex in response to acoustic signals introduced into the first conduit, the second conduit enclosing a material and/or a pressure that is different from that in the first conduit, such that an acoustic signal travelling from the inlet to the outlet of the first conduit is affected by the flexing of the membrane suppress or enhance characteristics of the acoustic signal.

2. The device of claim 1, wherein the membrane is made of plastic.

3. The device of claim 1, wherein the second conduit has an acoustic inlet, but no acoustic outlet.

4. The device of claim 1, wherein the second conduit has an acoustic outlet, but no acoustic inlet.

5. The device of claim 1, wherein the second conduit has an acoustic inlet and an acoustic outlet.

6. The device of claim 1, wherein the second conduit has neither an acoustic inlet nor an acoustic outlet.

7. The device of claim 1, wherein the first conduit has air at ambient conditions.

8. The device of claim 7, wherein the second conduit houses a gas other than air.

9. The device of claim 7, wherein the second conduit houses a liquid.

10. The device of claim 7, wherein the second conduit houses a semi-solid material.

11. The device of claim 7, wherein the second conduit houses air at a pressure different from ambient conditions.

12. The device of claim 1, further comprising a support member that is relatively rigid compared to the flexible membrane and that is provided between the first conduit and the second conduit for supporting an object, the device further comprising an acoustic signal source at the inlet end of the first conduit, and an acoustic signal detector at the outlet end of the conduit.

13. The device of claim 1, wherein the second conduit has an inlet for receiving a fluid and an outlet for providing a fluid, the device further including an acoustic source at the inlet end of the first conduit, and an acoustic detector at the outlet end of the first conduit, wherein the source and detector are used to determine changes in the fluid that is provided to the second conduit through the inlet to the second conduit based on changes in the detected acoustic signal.

14. The device of claim 1, further comprising an ultrasonic source at the inlet end of the first conduit.

15. The device of claim 14, wherein the first and second conduits are made sufficiently small to be usable as a catheter in a living body.

16. The device of claim 1, further comprising a subsonic source at the inlet end of the first conduit.

17. The device of claim 1, wherein the second conduit has an inlet for receiving a fluid and an outlet for providing a fluid, the device further including an acoustic source for providing acoustic energy at the inlet end of the first conduit, wherein the energy from the acoustic source is sufficient to measurably alter the characteristics of the fluid.

18. The device of claim 1, wherein the second conduit has a diaphragm at an inlet end, the device further comprising a single acoustic source for providing acoustic signals to both the first and second conduits.

19. The device of claim 1, wherein the second conduit has a diaphragm at an inlet end, the device further comprising a first and second separate acoustic sources for providing acoustic signals to the first and second conduits, respectively.

20. The device of claim 1, wherein the first conduit has a blind end at the outlet, such that the acoustic signal is reflected back from the outlet end.

21. The device of claim 1, wherein the first conduit has a diaphragm at the outlet, such that the acoustic signal is reflected back from the outlet end and is also provided out by the diaphragm.

22. A loudspeaker comprising:

a housing;

a flexible membrane in the housing and defining first and second regions within the housing, the first region being at ambient conditions, and the second region enclosing a material and/or a pressure that is different from the respective material and/or pressure in the first region; and a speaker in the first region;

wherein the membrane is sufficiently flexible to flex in response to sounds received from the speaker, and wherein sound from the speaker in the first region is altered by the flexing of the membrane and the alteration depends on the material and/or pressure in the second region before the sound altered by the membrane is provided to a listener.

23. A loudspeaker comprising:

a housing;

a flexible membrane in the housing and defining first and second regions within the housing, the first region being at ambient conditions, and the second region enclosing a material and/or a pressure that is different from the respective material and/or pressure in the first region; and a speaker in the second region;

wherein the membrane is sufficiently flexible to flex in response to sounds received from the speaker, and wherein sound from the speaker in the second region is altered by the flexing of the membrane and the flexing depends on the material and/or pressure in the second region.

24. A device comprising:

a first conduit having an inlet and an outlet;

an acoustic source for providing an acoustic signal to the inlet of the first conduit;

a second conduit that shares a common wall with the first conduit, the common wall being made from a flexible membrane that is sufficiently flexible to flex in response to the acoustic signal from the acoustic source, the second conduit being sealed from the first conduit and having a material and/or pressure that is different from the material and/or pressure in the first conduit; and an acoustic detector at the outlet of the first conduit, wherein sound traveling from the acoustic source to the outlet of the first conduit is affected by the flexing of the membrane, and wherein the characteristics of the flexing depends on the material and/or pressure in the second conduit.

25. A method comprising:

forming an acoustic device with a first conduit and a second conduit that share a common wall made from a flexible membrane that is sufficiently flexible to flex in response to the introduced acoustic signal from the acoustic source, providing in the second conduit a material and/or a pressure that is different from the material and/or pressure in the first conduit;

introducing an acoustic signal into the first conduit;

detecting at an outlet of the first conduit the acoustic signal from the acoustic source, wherein the detected signal is affected by the flexing of the membrane, wherein the flexing depends on the material and/or pressure selected for use in the second conduit.

26. The method of claim 25, further comprising a step of providing in the first conduit an object to be sensed, wherein the detected sound determines some characteristic of the object to be sensed.

27. The method of claim 26, wherein the detection is performed over time to determine a change in a characteristic of the object to be sensed.

28. The method of claim 25, further comprising a step of circulating a fluid in the second conduit, wherein the detected sound is used to determine a change in a characteristic of the fluid in the second conduit.

29. A device to be propelled through a fluid, the device comprising:
   a housing defining a first chamber and including a diaphragm;
   a source of acoustic energy for causing the diaphragm to flex in response to the acoustic energy; and
   a first compartment defining a second chamber within the first chamber, the first compartment housing a material different from that in the first chamber and having an exterior shell that includes a material that is sufficiently flexible to flex in response to the acoustic energy, the material being selected to affect a characteristic of the acoustic energy.

30. The device of claim 29, further comprising a second compartment having a flexible shell and enclosing a material selected to affect a characteristic of the acoustic energy.

31. An acoustic device comprising:
   a first conduit having an inlet end and an outlet end;
   a second conduit that shares a common wall with the first conduit, the common wall being made from a flexible membrane sufficiently flexible to flex in response to acoustic signals introduced into the first conduit, the second conduit enclosing a material and/or a pressure that is different from that in the first conduit, such that an acoustic signal travelling from the inlet to the outlet of the first conduit is affected by the flexing of the membrane suppress or enhance characteristics of the acoustic signal, wherein the second conduit has an acoustic inlet and no acoustic outlet.

32. The device of claim 31, wherein the second conduit houses a gas other than air.

33. The device of claim 31, wherein the second conduit houses a liquid.

34. The device of claim 31, wherein the second conduit houses a semi-solid material.

35. The device of claim 31, wherein the second conduit houses air at a pressure different from ambient conditions.

36. An acoustic device comprising:
   a first conduit having an inlet end and an outlet end;
   a second conduit that shares a common wall with the first conduit, the common wall being made from a flexible membrane sufficiently flexible to flex in response to acoustic signals introduced into the first conduit, the second conduit enclosing a material and/or a pressure that is different from that in the first conduit, such that an acoustic signal travelling from the inlet to the outlet of the first conduit is affected by the flexing of the membrane suppress or enhance characteristics of the acoustic signal, wherein the second conduit has an acoustic inlet and an acoustic outlet.

37. The device of claim 36, wherein the second conduit houses a gas other than air.

38. The device of claim 36, wherein the second conduit houses a liquid.

39. The device of claim 36, wherein the second conduit houses a semi-solid material.

40. The device of claim 36, wherein the second conduit houses air at a pressure different from ambient conditions.

41. An acoustic device comprising:
   a first conduit having an inlet end and an outlet end;
   a second conduit that shares a common wall with the first conduit, the common wall being made from a flexible membrane sufficiently flexible to flex in response to acoustic signals introduced into the first conduit, the second conduit enclosing a material and/or a pressure that is different from that in the first conduit, such that an acoustic signal travelling from the inlet to the outlet of the first conduit is affected by the flexing of the membrane suppress or enhance characteristics of the acoustic signal, wherein the second conduit has an acoustic outlet and no acoustic inlet.

42. The device of claim 41, wherein the second conduit houses a gas other than air.

43. The device of claim 41, wherein the second conduit houses a liquid.

44. The device of claim 41, wherein the second conduit houses a semi-solid material.

45. The device of claim 41, wherein the second conduit houses air at a pressure different from ambient conditions.

* * * * *